United States Patent
Kim et al.

(10) Patent No.: US 7,572,923 B2
(45) Date of Patent: Aug. 11, 2009

(54) INDIRUBIN DERIVATIVES HAVING ANTICANCER PROPERTY AGAINST HUMAN CANCER CELL LINE

(75) Inventors: Yong-Chul Kim, Gwangju (KR); Si Wouk Kim, Gwangju (KR); Tae Sung Kim, Gwangju (KR); Sang Kook Lee, Seoul (KR); Jae Il Kim, Gwangju (KR); Jung-Hoon Yoon, Gwangju (KR); Sang-Gun Ahn, Gwangju (KR); Myoung Ju Moon, Daegu (KR)

(73) Assignee: Anygen Co., Ltd., Gwangju (KR)

( * ) Notice: Subject to any disclaimer, the term of this patent is extended or adjusted under 35 U.S.C. 154(b) by 96 days.

(21) Appl. No.: 10/586,780

(22) PCT Filed: Jan. 26, 2005

(86) PCT No.: PCT/KR2005/000209

§ 371 (c)(1),
(2), (4) Date: Jul. 21, 2006

(87) PCT Pub. No.: WO2005/070416

PCT Pub. Date: Aug. 4, 2005

(65) Prior Publication Data

US 2007/0155816 A1 Jul. 5, 2007

(30) Foreign Application Priority Data

Jan. 27, 2004 (KR) ............ 10-2004-0005114

(51) Int. Cl.
C07D 209/34 (2006.01)
A61K 31/4015 (2006.01)

(52) U.S. Cl. .............. 548/457; 548/459; 548/460; 514/414

(58) Field of Classification Search ......... 548/457, 548/459

See application file for complete search history.

(56) References Cited

U.S. PATENT DOCUMENTS

2007/0276025 A1* 11/2007 Meijer et al. ............... 514/414

OTHER PUBLICATIONS

RN 301323-91-1 retrieved from CAPLUS on Jan. 14, 2008.*
RN 301323-78-4 retrieved from CAPLUS on Jan. 14, 2008.*
Cancer and Metastasis Reviews (1998),17(1), 91-106.*
Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online], [retrieved on Jul. 6, 2007]. Retrieved from the Internet, URL; http://en.wikipedia.org/wiki/Cancer>.*

* cited by examiner

*Primary Examiner*—Kamal A Saeed
*Assistant Examiner*—Shawquia Young
(74) *Attorney, Agent, or Firm*—Kenyon & Kenyon LLP

(57) ABSTRACT

The present invention relates to an indirubin derivative having anticancer property by inhibiting cell proliferation as to human cancer cell line. More particularly, this invention provides the synthesis of indirubin derivative known as CDK (Cyclin-dependent kinase) inhibitor. Further, inhibition activity of proliferation as to human cancer cell line and apoptosis against induced-differentiation of said indirubin derivative are researched to develop a novel indirubin derivative having efficacious anticancer properties as to various human cell lines.

9 Claims, 8 Drawing Sheets

INDIRUBIN DERIVATIVES HAVING ANTICANCER PROPERTY AGAINST HUMAN CANCER CELL LINE

INCORPORATION BY REFERENCE

This is a 371 national phase application of PCT/KR2005/000209 filed 26 Jan. 2005, claiming priority to Korean Patent Application No. 10-2004-0005114 filed 27 Jan. 2004, the contents of which are incorporated herein by reference.

TECHNICAL FIELD

The present invention relates to an indirubin derivative having anti-cancer property to human cancer cell line and property for inducing apoptosis to leukemia cell line by inducing differentiation. More particularly, this invention relates to an indirubin derivative as CDK (cyclin-dependent kinase) inhibitor having anti-cancer property by inhibiting proliferation of human cancer cell line and property for inducing apoptosis to leukemia cell line by inducing differentiation.

BACKGROUND ART

The agent for inducing differentiation of human cancer cell line has a handicap to be used as anti-cancer agent due to its high toxicity. Therefore, the present invention developed an indirubin derivative to be administered in combination with conventional differentiation inducing agent to show the synergic effect for apoptosis of human cancer cell line in a small amount.

Indirubin, one of active ingredients of Chinese herb drug, has been known as anti-cancer property against human cancer cell line. Hoessel et al. disclosed that indirubin is one of CDK (Cyclin-dependent kinase) inhibitor [*Nature Cell Biology* Vol. 1 May (1999)].

In Korean laying open patent publication No. 2000-6570 'Extract of physiological product', the process for extracting indirubin from indigo plant has been disclosed. Further, in Korean laying open patent publication No. 1998-25557 'Process for preparing indirubin using high concentration cell culture', the process for preparing indirubin in bio-reactor has been disclosed.

Also, the inventors also disclosed a biological process for preparing indirubin using recombinant *E. coli* harboring novel oxygenase gene in Korean laying open patent publication No. 2003-36580.

In this invention, numerous indirubin derivatives have been synthesized for detecting anti-cancer property of each derivative for selecting the efficacious compound. Through this experiment, novel indirubin derivative has found having excellent anti-cancer property in very low concentration level.

DISCLOSURE OF INVENTION

The object of the present invention is to provide an indirubin compound having anti-cancer property to human cancer cell line and property for inducing apoptosis to leukemia cell line by inducing differentiation as CDK inhibitor representing the following formulas (I)~(VII).

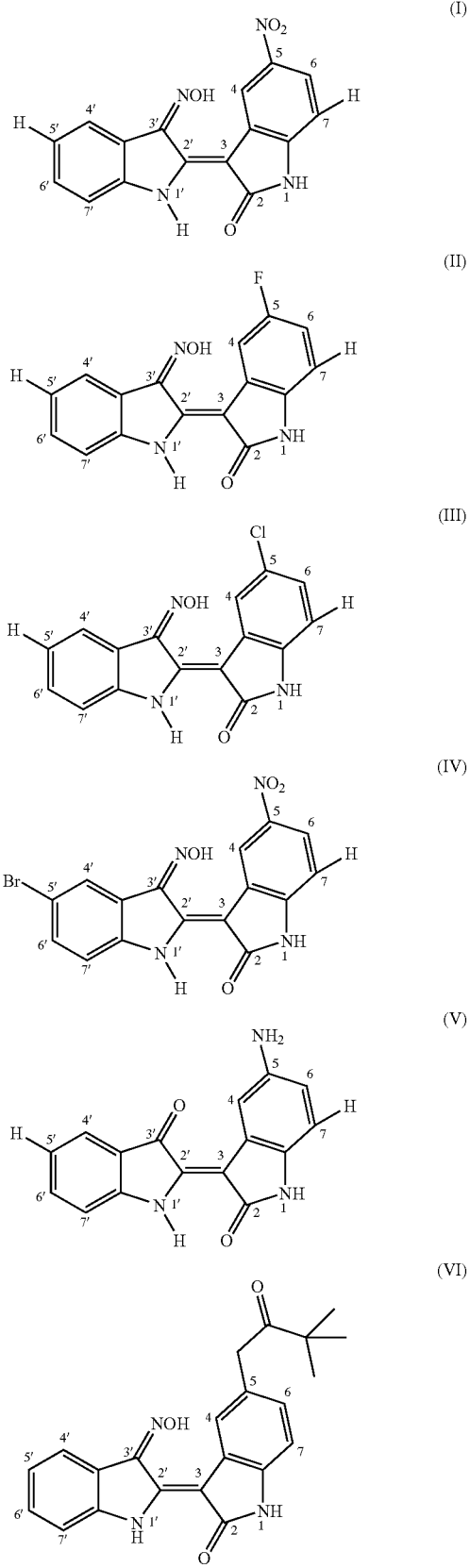

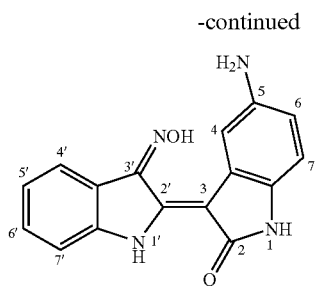

(VII)

Further, another object of the present invention is to provide an anti-cancer composition comprising 0.1~80 wt % of at least one compounds represented by above formulas (I)~(VII) and pharmaceutically acceptable carrier.

Further, the formulation of said anti-cancer composition is injection, capsule, tablet, solution or pellet.

BEST MODE FOR CARRYING OUT THE INVENTION

Figure 1:
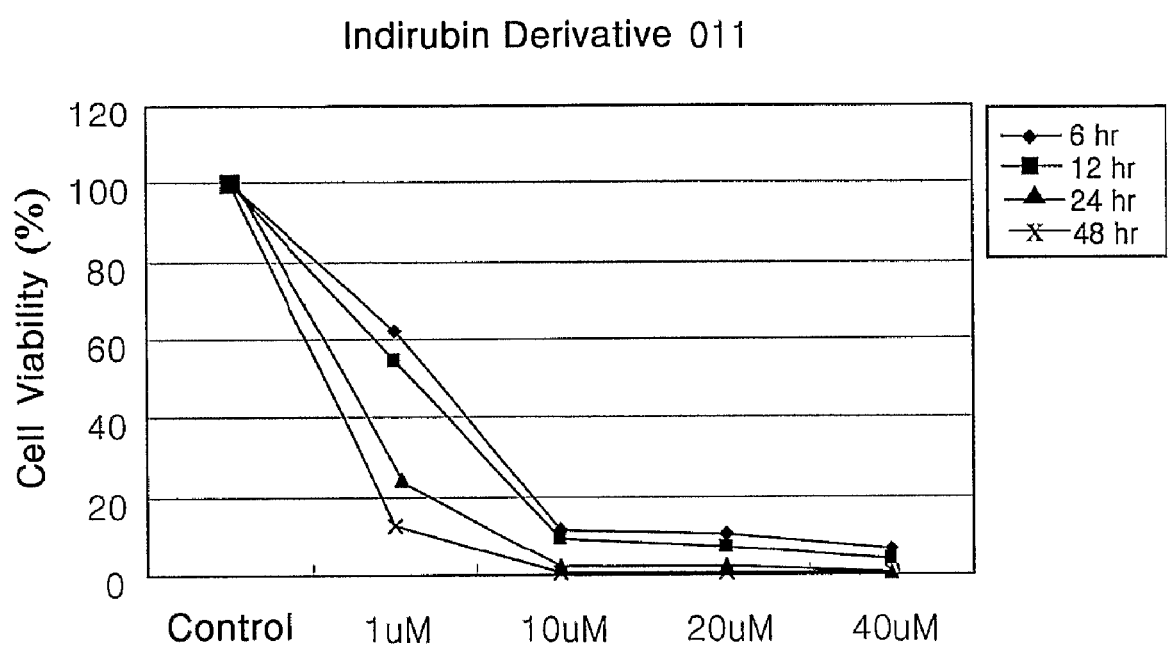
FIG. 1 is a diagram indicating the decline of cell viability according to the increase of compound concentration of indirubin derivative 011 represented by formula (I).

We would explain the preparation method of indirubin derivative of the present invention as follows.

1. Synthesis of Indirubin Derivative

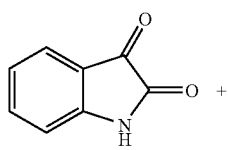

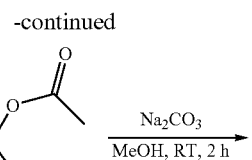

In 50 ml of round flask, indoxyl acetate (176 mg, 1 mmol) is added and dissolved with methanol (5 ml). After adding isatin (148 mg, 1 mmol) and Na$_2$CO$_3$ (265 mg, 2.5 mmol), the mixture is stirred for 2 hours at room temperature. Using TLC (Rf=0.4 ethyl acetate/hexane 1/2 v/v), the termination of reaction is confirmed. Obtained crude material is stored in refrigerator until crystalline aggregate is obtained. After formation of crystalline product, it is filtered. Final product is washed with methanol and water several times. After drying in vacuum pump, violet color solid (157.6 mg) is obtained in 60.2% yield.

2. Synthesis of Indirubin Oxime Derivative

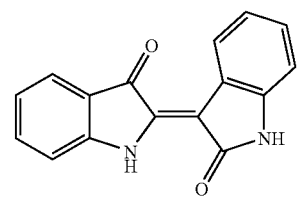

Indirubin (262 mg, 1 mmol) is laid on 50 ml of two neck round flask. It is dissolved with pyridine (5 ml) and H$_2$NOH.HCl (181 mg, 2.6 mmol) is added. The mixture is refluxed for 2 hours at more than 120° C. Using TLC (Rf=0.45 ethyl acetate/hexane 1/1 v/v), the termination of reaction is confirmed. Then, the temperature of reaction solution declines to room temperature. 1N HCl (50~100 ml) is added to obtained crude material and the obtained crystalline product is filtered. Then, crystalline product is dissolved with 1N NaOH (50 ml). After dissolving obtained product, dark violet solid (263.5 mg) is obtained by recrystallization in 1N HCl (100 ml) at 93% yield.

3. Synthesis of Indirubin Hydrazone Derivative

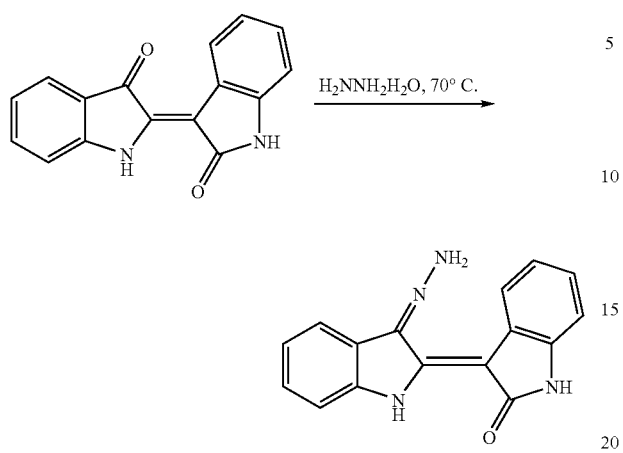

Indirubin (80 mg, 0.3 mmol) is laid on 50 ml of two neck round flask. After adding $H_2NNH_2 \cdot H_2O$, the reaction mixture is heated until 70~80° C. Blue color solid is formed after 1 day and it is filtered and washed with ether. For purification, the obtained product is dissolved with NMP. Then, purified product is obtained after silica gel column chromatography with eluent(ethyl acetate/hexane:1/1). At this step, NMP has to be removed by washing with hexane several times. After removing the solvent using rotary evaporator, final product is obtained in 10% (8 mg) yield.

4. Synthesis of Indirubin N-acetyl Derivative

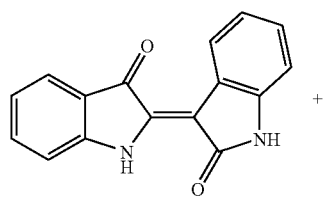

Indirubin (314.4 mg, 1.2 mmol) is laid on 50 ml of round flask. After adding acetic anhydride (15 ml), the mixture is refluxed for 10 hours. Using TLC (Rf=0.55 ethyl acetate/hexane 1/2 v/v), the termination of reaction is confirmed. The obtained material is filtered and washed with water several times. Then, it is dried in vacuum pump. Remaining filtered solution is freeze dried with removal of solvent to enhance the yield. Finally, the compound is obtained in 98% (358 mg) yield.

5. Synthesis of Indirubin Amine Derivative

Indirubin-5-nitro (500 mg, 1.629 mmol) is laid on 50 ml of two neck round flask. After adding DMF (5 ml) and $SnCl_2 \cdot 2H_2O$ (1.838 g, 8.145 mmol), the mixture is heated at 70° C. After one hour, using TLC (Rf=0.2 $CHCl_3$/MeOH 50/1 v/v), the termination of reaction is confirmed. After adding 1N NaOH until pH 11, the reaction solution is made into alkali. Obtained material is transferred to separate funnel. After extracting it using ethyl acetate, obtained material is washed with brine. Using rotary evaporator, the solvent is removed. Then, obtained crystalline material is dried in vacuum pump. Final material is obtained in 45.2% (204 mg) yield.

6. Synthesis of Indirubin Acyl Amide Derivative

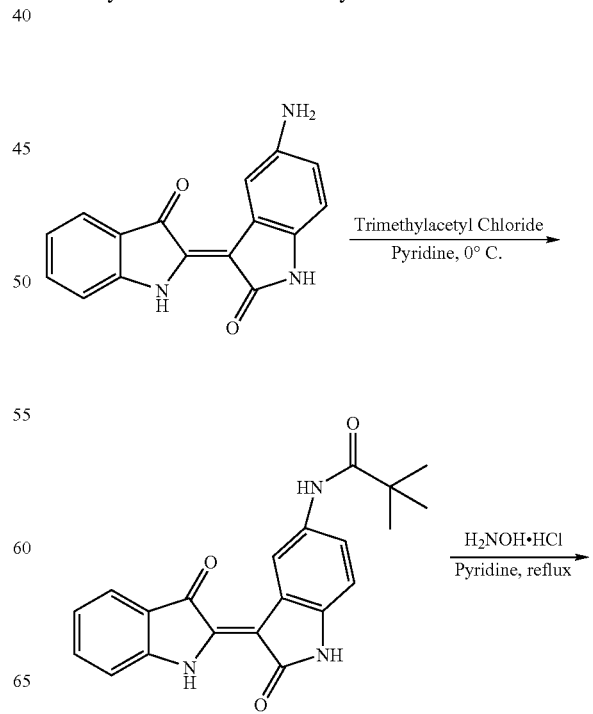

1 mM of indirubin-5-1NH$_2$ (AGM029) is dissolved with pyridine. 2 equivalent of trimethylacetyl chloride is added drop by drop at 0° C. The mixture is stirred for 30 minutes. Then, 5-NH-trimethyacetyl-indirubin with 6 equivalent of hydroxylamine hydrochloride is added to pyridine. The obtained mixture is refluxed for 2~3 hours at 80~90° C. After cooling the mixture, obtained material is neutralized with 1N HCl. Obtained precipitate is filtered and washed with water. Finally, 5-NH-trimethyl-indirubin-3-oxime (AGM030) is obtained.

The synthesized compound prepared by above steps can be represented by following formula.

AGM001~AGM031 compounds are prepared by substituting the group in $X_1$, $X_2$, Y, Z, and R position. The synthesized compounds are analyzed using $^1$H NMR (nucleic magnetic resonance) and MS (mass spectroscopy). Followings are NMR and MS data of prepared compounds in the present invention.

Synthesis of AGM001 Compound 1H,1'H-[2,3'] biindolylidene-3,2'-dione (AGM 001)

$^1$H NMR(600 MHz, CDCl$_3$) δ(ppm) 11.00(1H, s, N—H), 10.87(1H, s, N'—H), 8.76(1H, d, J=7.4 Hz), 7.64(1H, d, J=7.3 Hz), 7.56(1H, t, J=7.8 Hz), 7.41(1H, d, J=7.8 Hz), 7.24(1H, t, J=7.3 Hz), 7.00(2H, m) 6.89(1H, d, J=7.4 Hz) MS(MALDI-TOF) m/z: 262.7

Synthesis of AGM002 Compound 1H,1'H-[2,3'] biindolylidene-3,2'-dione 3-oxime (AGM002)

$^1$H NMR(300 MHz, DMSO-d$_6$) δ(ppm) 13.49(1H, s, NOH) 11.74(1H, s, N'—H), 10.74(1H, s, N'—H), 8.65(1H, d, J=7.8 Hz), 8.11(1H, d, J=7.8 Hz), 7.20(2H, m), 7.13(1H, t, J=7.5 Hz), 6.97(4H, m) MS(MALDI-TOF) m/z: 276.7

Synthesis of AGM006 Compound 1-acetyl-1H,1'H-[2,3'] biindolylidene-3,2'-dione (AGM006)

$^1$H NMR(300 MHz, DMSO-d$_6$) δ(ppm) 10.52(1H, s, N'—H), 9.00(1H, dd, J=7.8, 1.5 Hz), 8.29(1H, d, J=7.5 Hz), 7.73(1H, d, J=7.5 Hz), 7.62(1H, t, J=7.5 Hz), 7.31(2H, m), 7.03(2H, m) MS(MALDI-TOF) m/z: 304.2

Synthesis of AGM009 Compound

5'-nitro-1H,1'H-[2,3'] biindolylidene-3,2'-dione (AGM009)

$^1$H NMR(300 MHz, DMSO-d$_6$) δ(ppm) 11.25(1H, br s, N—H), 11.20(1H, br s, N'—H), 9.64(1H, s), 8.15(1H, dd, J=2.3, 8.4 Hz), 7.63(2H, m), 7.42(1H, d, J=7.8 Hz), 7.05(2H, m) MS(MALDI-TOF) m/z: 307.8

Synthesis of AGM010 Compound

5'-fluoro-1H,1'H-[2,3'] biindolylidene-3,2'-dione (AGM010)

$^1$H NMR(300 MHz, DMSO-d$_6$) δ(ppm) 11.10(1H, br s, N—H), 10.92(1H, br s, N'—H), 8.58(1H, dd, J=2.7, 7.8 Hz), 7.62(2H, m), 7.43(1H, d, J=8.1 Hz), 7.00(3H, m) MS(MALDI-TOF) m/z: 280.6

Synthesis of AGM011 Compound

5'-nitro-1H,1'H-[2,3'] biindolylidene-3,2'-dione 3-oxime (AGM011)

$^1$H NMR(300 MHz, DMSO-d$_6$) δ(ppm) 13.92(1H, s, NOH) 11.90(1H, s, N—H), 11.44(1H, s, N'—H), 9.47(1H, s), 8.27(1H, d, J=7.5 Hz), 8.10(1H, dd, J=2.3, 8.4 Hz), 7.48(2H, m), 7.09(2H, m) MS(MALDI-TOF) m/z: 321.0

Synthesis of AGM012 Compound

5'-fluoro-1H,1'H-[2,3'] biindolylidene-3,2'-dione 3-oxime (AGM012)

$^1$H NMR(300 MHz, DMSO-d$_6$) δ(ppm) 13.66(1H, s, NOH) 11.80(1H, S, N—H), 10.75(1H, s, N'—H), 8.48(1H, dd, J=2.6, 11.3 Hz), 8.23(1H, d, J=7.5 Hz), 7.43(2H, m), 7.00(3H, m) MS(MALDI-TOF) m/z: 295.2

Synthesis of AGM013 Compound

5'-methyl-1H,1'H-[2,3'] biindolylidene-3,2'-dione 3-oxime (AGM013)

$^1$H NMR(300 MHz, DMSO-d$_6$) δ(ppm) 13.40(1H, s, NOH) 11.72(1H, s, N—H), 10.59(1H, s, N'—H), 8.43(1H, s), 8.24 (1H, d, J=7.5 Hz), 7.39(2H, m), 7.00(2H, m), 6.77(1H, d, J=7.8 Hz), 2.34(3H, s, CH3) MS(MALDI-TOF) m/z: 291.7

Synthesis of AGM014 Compound

5'-chloro-1H,1'H-[2,3'] biindolylidene-3,2'-dione 3-oxime (AGM014)

$^1$H NMR(300 MHz, DMSO-d$_6$) δ(ppm) 13.68(1H, s, NOH) 11.83(1H, s, N—H), 10.85(1H, s, N'—H), 8.65(1H, s), 8.24(1H, d, J=7.5 Hz), 7.42(2H, m), 7.10(2H, m), 6.88(1H, d, J=8.1 Hz) MS(MALDI-TOF) m/z: 311.6

Synthesis of AGM015 Compound

5'-iodo-1H,1'H-[2,3'] biindolylidene-3,2'-dione 3-oxime (AGM015)

$^1$H NMR(300 MHz, DMSO-d$_6$) δ(ppm) 13.67(1H, s, NOH) 11.83(1H, s, N—H), 10.84(1H, s, N'—H), 8.90(1H, s), 8.25(1H, d, J=7.8 Hz), 7.40(3H, m), 7.06(1H, s), 6.74(1H, d, J=7.8 Hz) MS(MALDI-TOF) m/z: 403.7

Synthesis of AGM016 Compound

5',7'-dimethyl-1H,1'H-[2,3'] biindolylidene-3,2'-dione 3-oxime (AGM016)

$^1$H NMR(300 MHz, DMSO-d$_6$) δ(ppm) 13.38(1H, s, NOH) 11.77(1H, s, N—H), 10.62(1H, s, N'—H), 8.34(1H, s), 8.24(1H, d, J=7.5 Hz), 7.39(2H, m), 7.02(1H, s), 6.77(1H, s), 2.31(3H, s, CH$_3$) 2.22(3H, s, CH$_3$) MS(MALDI-TOF) m/z: 305.8

Synthesis of AGM017 Compound

5'-chloro-7'-methyl-1H,1'H-[2,3'] biindolylidene-3,2'-dione 3-oxime (AGM017)

$^1$H NMR(300 MHz, DMSO-d$_6$) δ(ppm) 13.65(1H, s, NOH) 11.88(1H, s, N—H), 10.88(1H, s, N'—H), 8.52(1H, s), 8.24(1H, d, J=7.4 Hz), 7.43(2H, m), 7.04(2H, m) 2.22(3H, s, CH$_3$) MS(MALDI-TOF) m/z: 325.6

Synthesis of AGM018 Compound 5-bromo-1H,1'H-[2,3'] biindolylidene-3,2'-dione 3-oxime (AGM018)

$^1$H NMR(300 MHz, DMSO-d$_6$) δ(ppm) 13.74(1H, s, NOH) 11.75(1H, s, N—H), 10.75(1H, s, N'—H), 8.61(1H, d, J=10.2 Hz), 8.32(1H, s), 7.57(1H, d, J=7.8 Hz) 7.41(1H, d, J=7.5 Hz) 7.14(1H, t, J=2.1, 7.8 Hz) 6.92(2H, m) MS(MALDI-TOF) m/z: 356.6

Synthesis of AGM019 Compound 3,2'-dioxo-1,3,1',2'-tetrahydro-[2,3'] biindolylidene-5'-sodium sulfonate (AGM019)

$^1$H NMR(300 MHz, DMSO-d$_6$) δ(ppm) 11.03(1H, s, N—H), 10.95(1H, S, N'—H), 9.11(1H, s), 7.66(1H, d, J=7.5 Hz), 7.55(2H, m), 7.42(1H, d, J=8.1 Hz), 7.04(1H, t, J=7.5 Hz), 6.82(1H, d, J=8.1 Hz) MS(MALDI-TOF) m/z: 364.6

Synthesis of AGM020 Compound 3-hydroxyimino-2'-oxo-1,3,1',2'-tetrahydro-[2,3'] biindolylidene-5'-sodium sulfonate (AGM020)

$^1$H NMR(300 MHz, DMSO-d$_6$) δ(ppm) 13.70(1H, s, NOH) 11.81(1H, s, N—H), 10.79(1H, s, N'—H), 8.87(1H, s), 8.25(1H, d, J=7.5 Hz), 7.43(3H, m) 7.03(1H, m) 6.90(1H, d, J=7.8 Hz) MS(MALDI-TOF) m/z: 380.3

Synthesis of AGM021 Compound 5-bromo-1H,1'H-[2,3'] biindolylidene-3,2'-dione (AGM021) $^1$H NMR(300 MHz, DMSO-d$_6$) δ(ppm) 11.11 (1H, s, N—H), 10.92(1H, s, N'—H), 8.75(1H, s), 7.74(2H, m), 7.40(1H, d, J=8.4 Hz), 7.27(1H, t, J=7.5 Hz), 7.02(1H, t, J=7.5 Hz), 6.89(1H, d, J=7.5 Hz) MS(MALDI-TOF) m/z: 341.5

Synthesis of AGM023 Compound 5-bromo-5'-nitro-1H,1'H-[2,3'] biindolylidene-3,2'-dione 3-oxime (AGM023)

$^1$H NMR(300 MHz, DMSO-d$_6$) δ(ppm) 14.17(1H, s, NOH), 11.90(1H, s, N—H), 11.42(1H, s, N'—H), 9.43(1H, s), 8.36(1H, s), 8.10(1H, d, J=8.4 Hz), 7.60(1H, d, J=7.8 Hz), 7.45(1H, d, J=8.4 Hz), 7.05(1H, d, J=8.4 Hz) MS(MALDI-TOF) m/z: 401.8

Synthesis of AGM024 Compound

5'-methyl-1H,1'H-[2,3'] biindolylidene-3,2'-dione (AGM024)

1H NMR(300 MHz, DMSO-d$_6$) δ(ppm) 10.92(2H, br s, NH &N'H), 8.62(1H, s), 7.60(2H, m), 7.41(1H, d, J=7.5 Hz), 7.03(2H, m), 6.78(1H, s, J=7.8 Hz) 2.32(3H, s, CH$_3$) MS(MALDI-TOF) m/z: 276.4

Synthesis of AGM025 Compound

5'-chloro-1H,1'H-[2,3'] biindolylidene-3,2'-dione (AGM025)

$^1$H NMR(300 MHz, DMSO-d$_6$) δ(ppm) 11.11(1H, s, N—H), 11.00(1H, s, N'—H), 8.79(1H, s), 7.62(2H, m), 7.42 (1H, d, J=8.1 Hz), 7.28(1H, dd, J=2.1, 8.4 Hz), 7.04(1H, t, J=7.4 Hz), 6.90(1H, d, J=8.1 Hz) MS(MALDI-TOF) m/z: 296.5

Synthesis of AGM026 Compound

5'-iodo-1H,1'H-[2,3'] biindolylidene-3,2'-dione (AGM026) $^1$H NMR(300 MHz, DMSO-d$_6$) δ(ppm) 11.07 (2H, br s, NH & N'H), 9.11(1H, s), 7.61(3H, m), 7.42(1H, d, J=8.1 Hz), 7.04(1H, t, J=7.8 Hz), 6.75(1H, d, J=8.1 Hz) MS(MALDI-TOF) m/z: 388.5

Synthesis of AGM027 Compound

5',7'-dimethyl-1H,1'H-[2,3'] biindolylidene-3,2'-dione (AGM027)

$^1$H NMR(300 MHz, DMSO-d$_6$) δ(ppm) 11.03(1H, br s, N—H), 10.83(1H, br s, N'—H), 8.48(1H, s), 7.59(2H, m), 7.40(1H, br s), 7.00(1H, br s), 6.88(1H, br s) 2.23(6H, m, 5',7' CH$_3$) MS(MALDI-TOF) m/z: 290.7

Synthesis of AGM028 Compound

5'-chloro-7'-methyl-1H,1'H-[2,3'] biindolylidene-3,2'-dione (AGM028)

$^1$H NMR(300 MHz, DMSO-d$_6$) δ(ppm) 11.11(1H, s, N—H), 11.04(1H, s, N'—H), 8.64(1H, s), 7.60(2H, m), 7.42 (1H, d, J=7.8 Hz), 7.12(1H, s), 7.03(1H, t, J=7.5 Hz) 2.22(3H, s, CH$_3$) MS(MALDI-TOF) m/z: 310.7

Synthesis of AGM029 Compound

5'-amino-1H,1'H-[2,3'] biindolylidene-3,2'-dione (AGM029)

$^1$H NMR(300 MHz, DMSO-d$_6$) δ(ppm) 10.95(1H, s, N—H), 10.45(1H, s, N'—H), 8.15(1H, s), 7.58(2H, m), 7.39 (1H, d, J=8.1 Hz), 7.00(1H, t, J=7.5 Hz) 6.56(2H, m), 4.75 (2H, s, NH$_2$) MS(MALDI-TOF) m/z: 276.9

Synthesis of AGM030 Compound

5-NH-trimethylacetyl-indirubin-3-oxime (AGM030)

NMR(300 MHz, DMSO-d$_6$) δ(ppm) 13.40(1H, s, NOH) 11.73(1H, s, N'—H), 10.67(1H, s, N—H), 8.89(1H, s, amide-NH), 8.46(1H, s), 8.25(1H, d, J=7.5 Hz), 7.40(2H, m), 7.24 (1H, d, J=8.4 Hz), 7.03(1H, m), 6.81(1H, d, J=8.4 Hz), 1.26 (9H, s, (CH$_3$)$_3$) MS(MALDI-TOF) m/z: 376

Synthesis of AGM031 Compound

5'-amino-1H,1'H-[2,3'] biindolylidene-3,2'-dione-3-oxime (AGM031)

$^1$H NMR(300 MHz, DMSO-d$_6$) δ(ppm) 13.40(1H, s, NOH) 10.96(1H, s, N—H), 10.43(1H, s, N'—H), 8.15(1H, s), 7.55(2H, m), 7.40(1H, d, J=8.1 Hz), 7.01(1H, t, J=7.5 Hz) 6.54(2H, m), 4.73(2H, s, NH$_2$) MS(MALDI-TOF) m/z: 290.8

The forms of substituting groups $X_1$, $X_2$, Y, Z and R of compounds AGM001~AGM031 are described in following Table 1.

TABLE 1

|  | X1 | X2 | Y | Z | R |
|---|---|---|---|---|---|
| AGM001 | H | H | O | H | H |
| AGM002 | H | H | NOH | H | H |
| AGM003 | CF$_3$O | H | O | H | H |
| AGM004 | CF$_3$O | H | NOH | H | H |
| AGM005 | H | H | NNH$_2$ | H | H |
| AGM006 | H | H | O | H | CH$_3$CO |
| AGM007 | H | H | O | Br | CH$_3$CO |
| AGM008 | CF$_3$O | H | O | H | CHO$_3$CO |
| AGM009 | NO$_2$ | H | O | H | H |
| AGM010 | F | H | O | H | H |
| AGM011 | NO$_2$ | H | NOH | H | H |
| AGM012 | F | H | NOH | H | H |
| AGM013 | CH$_3$ | H | NOH | H | H |
| AGM014 | Cl | H | NOH | H | H |
| AGM015 | I | H | NOH | H | H |
| AGM016 | CH$_3$ | CH$_3$ | NOH | H | H |
| AGM017 | Cl | CH$_3$ | NOH | H | H |
| AGM018 | H | H | NOH | Br | H |
| AGM019 | SO$_3$—Na+ | H | O | H | H |
| AGM020 | SO$_3$—Na+ | H | NOH | H | H |
| AGM021 | H | H | O | Br | H |
| AGM022 | NO$_2$ | H | O | Br | H |
| AGM023 | NO$_2$ | H | NOH | Br | H |
| AGM024 | CH$_3$ | H | O | H | H |
| AGM025 | Cl | H | O | H | H |
| AGM026 | I | H | O | H | H |
| AGM027 | CH$_3$ | H | O | H | H |
| AGM028 | Cl | H | O | H | H |
| AGM029 | NH$_2$ | H | O | H | H |
| AGM030 | NHCO$^t$Bu | H | O | H | H |
| AGM031 | NH$_2$ | H | NOH | H | H |

The present invention will be more specifically explained by the following examples. However, it should be understood that the examples are intended to illustrate but not in any manner to limit the scope of the present invention.

EXAMPLES

Example 1

Analysis of Inhibition Effect to Cancer Cell Line Proliferation by Indirubin Derivative To detect the influence against human cancer cell line proliferation by indirubin derivative, human lung cancer cell line (A549), human stomach cancer cell line (SNU-638), human colon cancer cell line (Col2), human abdominal cavity cancer cell line (HT 1080) and human leukemia cell line (HL-60) are employed in vitro test.

For measuring the proliferation inhibition by indirubin compound, the method disclosed in K. Likhitwitayawuid et al. *Journal. Nat. Prod.* 58(1993) 1468-1478 is employed. Followings are simple description of this method. The cancer cell line is diluted into $5 \times 10^4$ cfu/ml. Then, various concentrations of test compounds are added to 96 well microtiter plate containing diluted cell line. After incubating test plate for 3~4 days at 37° C., the test plate is dried and Tris-base is added. Then, using ELISA plate detector, the absorbance at 515 nm is measured. $IC_{50}$ is measured by non-linear regression method. Proliferation inhibition against cancer cell line by indirubin derivative is shown in Table 2.

TABLE 2

Inhibition against cancer cell line proliferation by indirubin derivative

| Compound | $IC_{50}$ (Ma) | | | | |
|---|---|---|---|---|---|
| | A549 | SNU-638 | Col2 | HT108 | HL60 |
| AGM001 | 31.0 | >100 | >100 | 42.2 | |
| AGM002 | 62.0 | >100 | >100 | 4.8 | |
| AGM003 | >100 | >100 | >100 | | >100 |
| AGM004 | 9.6 | 23.1 | >100 | 32.1 | |
| AGM005 | 98.2 | >100 | >100 | 40.8 | |
| AGM006 | >100 | >100 | >100 | >100 | >100 |
| AGM007 | >100 | >100 | >100 | >100 | >100 |
| AGM008 | >100 | >100 | >100 | >100 | >100 |
| AGM009 | >100 | >100 | >100 | >100 | >100 |
| AGM010 | 96.8 | 40.3 | >100 | >100 | >100 |
| AGM011 | 5.43 | 1.21 | 25.5 | 5.87 | 9.23 |
| AGM012 | 13.2 | 2.06 | 64.2 | 3.41 | 89.3 |
| AGM013 | 20.4 | 17.6 | >100 | 36.7 | 65.4 |
| AGM014 | 12.1 | 6.22 | 16.8 | 10.8 | 4.81 |
| AGM015 | >100 | >100 | >100 | >100 | >100 |
| AGM016 | >100 | 90.6 | >100 | >100 | >100 |
| AGM017 | >100 | >100 | >100 | >100 | >100 |
| AGM018 | 38.6 | 32.9 | 10.5 | 73.6 | 25.0 |
| AGM019 | >100 | >100 | >100 | >100 | >100 |
| AGM020 | >100 | >100 | >100 | >100 | 47.0 |
| AGM021 | >100 | >100 | >100 | >100 | >100 |
| AGM022 | >100 | >100 | >100 | >100 | >100 |
| AGM023 | 23.2 | 12.06 | 44.2 | 4.41 | 69.3 |
| AGM024 | >100 | >100 | >100 | >100 | >100 |
| AGM025 | >100 | >100 | >100 | >100 | >100 |
| AGM026 | >100 | >100 | >100 | >100 | >100 |
| AGM027 | >100 | >100 | >100 | >100 | >100 |
| AGM028 | >100 | >100 | >100 | >100 | >100 |
| AGM029 | 33.2 | 21.06 | 31.2 | 5.41 | 59.3 |
| AGM030 | 6.40 | 6.52 | 13.92 | 4.18 | 21.28 |
| AGM031 | 9.13 | 10.03 | 24.55 | 5.07 | 12.95 |
| Ellipticin (positive control) | 0.28 | 1.99 | 1.71 | 3.59 | 3.13 |

From this experiment, AGM011, AGM012, AGM014, AGM023 and AGM029 are shown to be a effective inhibitor against proliferation of human cancer cell line.

Example 2

Analysis of Differentiation Inducing Effect to Leukemia Cell Line (HL-60) by Indirubin Derivative For measuring the differentiation inducing effect to acute bone merrow leukemia cell line (HL-60) by indirubin AGM compound, NBT (nitroblue tetrazolium) reduction reaction method is employed. The leukemia cell line is diluted into $2 \times 10^5$ cfu/ml. After treating 20 μM and 1 μM concentrations of test compounds, test plate is incubated for 3 days at 37° C. in 5% $CO_2$ incubator. Incubated cells are washed with phosphate buffered saline (PBS). Then, they are further incubated in PBS solution containing 0.1% NBT and 200 ng/ml of PMA (phorbol 12-myristate 13-acetate) for 30 minutes at 37° C. Incubated cells are centrifuged and collected cells are washed with PBS solution. Using cell number counter, differentiated cells forming nitroblue formazan among total cells are counted. As a result, we find that AGM029 excellently induces the differentiation at 20 μM concentration. Table 3 shows the percentage of inducing differentiation according to the concentration and kind of AGM compound.

TABLE 3

Percentage of inducing differentiation as to leukemia cell line HL-60 by indirubin derivative

| Compound | % of Differentiation | | |
|---|---|---|---|
| | 20 μM | 1 μM | 0.2 μM |
| Media | 1.80 ± 0.29 | 3.08 ± 1.29 | |
| 1 | 10.00 ± 0.27 | 7.76 ± 3.42 | |
| 2 | 6.78 ± 0.40 | 11.12 ± 0.31 | |
| 3 | 10.36 ± 0.29 | 6.27 ± 1.76 | |
| 4 | — | 22.81 ± 2.38 | |
| 6 | 10.49 ± 0.25 | 9.99 ± 1.47 | |
| 9 | 29.26 ± 1.59 | 19.94 ± 2.02 | |
| 10 | 13.01 ± 0.14 | 7.53 ± 1.02 | |
| 11 | — | — | 24.02 ± 0.85 |
| 12 | — | 32.71 ± 1.73 | |
| 13 | — | 26.22 ± 2.04 | |
| 14 | — | 40.97 ± 1.19 | |
| 15 | — | 30.50 ± 4.97 | |
| 16 | 10.35 ± 0.62 | 3.07 ± 1.69 | |
| 17 | 2.62 ± 0.23 | 8.37 ± 0.45 | |
| 18 | — | 8.69 ± 4.95 | |
| 19 | 12.44 ± 1.66 | 9.36 ± 0.13 | |
| 20 | 23.86 ± 1.31 | 11.34 ± 2.32 | |
| 21 | 9.64 ± 0.51 | 11.63 ± 3.48 | |
| 22 | 22.89 ± 0.51 | 18.35 ± 0.02 | |
| 23 | — | — | 18.38 ± 0.27 |
| 24 | 14.38 ± 0.42 | 24.89 ± 6.06 | |
| 25 | 14.40 ± 0.82 | 26.18 ± 0.59 | |
| 26 | 22.23 ± 0.60 | 29.84 ± 1.12 | |
| 27 | 4.75 ± 0.41 | 9.45 ± 0.92 | |
| 28 | 0.70 ± 0.16 | 8.85 ± 2.20 | |
| 29 | — | 45.05 ± 0.59 | |
| Indirubin | 1.18 ± 0.18 | 15.28 ± 1.12 | |

Next, we test if AGM compound of present invention can synergically induce the differentiation of acute bone merrow leukemia cell line when it is treated with low concentration of 1,25-dihydroxyvitamin D3[1,25-$(OH)_2D_3$] or all-trans retinoic acid (ATRA) known as differentiation inducing agent. The cells are incubated with 1 μM AMG and low concentration of 1,25-$(OH)_2D_3$ and ATRA capable of 30% induction of differentiation. After measuring by NBT reduction method, AGM010 and AGM029 show more than 70% of differentiation of cells which are induced by 1,25-$(OH)_2D_3$ and ATRA. Even though AGM023 shows some cytotoxicity, it shows high induction of differentiation when it is treated with 0.2

µM of conventional differentiation inducing agent. Table 4 show the results of percentage of differentiation as to human leukemia cell line when AGM compound is treated with 5 nM of 1,25-(OH)$_2$D$_3$ or 50 nM of ATRA. As a positive control, conventional differentiation inducing agent is used.

TABLE 4

Results of percentage of differentiation as to human leukemia cell line when AGM compound is treated with 5 nM of 1,25-(OH)$_2$D$_3$ or 50 nM of ATRA

| Compound | % of Differentiation | |
|---|---|---|
| | 1,25-(OH)$_2$D$_3$ | all-trans RA |
| 1 µM | | |
| Media | 19.21 ± 1.23 | 29.75 ± 2.65 |
| 1 | 28.36 ± 0.15 | 39.61 ± 1.25 |
| 2 | 24.52 ± 2.67 | 37.78 ± 1.06 |
| 3 | 22.04 ± 0.38 | 41.01 ± 1.26 |
| 4 | 26.36 ± 3.05 | 28.68 ± 0.23 |
| 6 | 19.60 ± 0.56 | 42.81 ± 1.05 |
| 9 | 48.51 ± 3.49 | 59.32 ± 1.54 |
| 10 | 78.44 ± 6.88 | 75.08 ± 6.80 |
| 11 | — | — |
| 12 | 24.29 ± 1.34 | 54.81 ± 1.65 |
| 13 | 35.49 ± 5.45 | 70.54 ± 2.17 |
| 14 | 21.72 ± 1.22 | 72.40 ± 3.05 |
| 15 | 33.27 ± 0.75 | 67.41 ± 1.36 |
| 16 | 27.24 ± 1.32 | 33.99 ± 0.47 |
| 17 | 22.10 ± 0.90 | 43.17 ± 1.56 |
| 18 | 36.52 ± 1.27 | 23.13 ± 0.71 |
| 19 | 27.66 ± 1.28 | 51.49 ± 0.13 |
| 20 | 23.34 ± 0.65 | 34.50 ± 2.91 |
| 21 | 24.64 ± 0.65 | 28.23 ± 0.02 |
| 22 | 48.28 ± 0.36 | 51.20 ± 3.70 |
| 23 | — | — |
| 24 | 41.66 ± 0.40 | 51.01 ± 0.88 |
| 25 | 49.41 ± 0.08 | 48.39 ± 1.48 |
| 26 | 44.43 ± 0.09 | 60.33 ± 0.51 |
| 27 | 21.74 ± 1.90 | 43.19 ± 1.73 |
| 28 | 35.22 ± 0.55 | 55.57 ± 1.11 |
| 29 | 79.03 ± 0.55 | 78.81 ± 0.77 |
| Indirubin | 26.39 ± 0.98 | 44.87 ± 2.54 |
| 0.2 µM | | |
| 11 | 31.79 ± 0.87 | 34.87 ± 0.74 |
| 23 | 89.76 ± 0.88 | 90.85 ± 0.36 |
| P control | 85.95 ± 1.43 | 90.33 ± 0.13 |

According to Example 1 and Example 2, AGM023 compound shows excellent anti-cancer property. Further, AGM011, AGM029, AGM012 and AGM014 also show excellent anti-cancer properties as to various human cancer cell lines. Therefore, we find that such 5 compounds have far enhanced anti-cancer properties which can be anticipated from conventional indirubin derivative.

Example 3

Measurement of Cell Viability After Indirubin Derivatives Treatment (011) in RK3E-Ras cells To measure the influence to cell viability by indirubin derivative, RK3E-Ras cell, 1×10$^5$/well is seeding on 24 well plate. After incubation of cells for 12~24 hours, indirubin derivative 011 in various concentration (1 µM, 10 µM, 20 µM, 40 µM) are treated for 6, 12, 24, 48 hours respectively. As control, cells without treating any compound are employed. After MTT assay, cell viability is rapidly declined according to the increase of concentration of indirubin derivative 011 represented by formula (I). FIG. 1 show the decline of cell viability after treatment of indirubin derivative 011.

Example 4

Measurements of DNA Fragmentation After Indirubin Derivatives Treatment (011) in RK3E-Ras cells We test if the decline of cell viability by indirubin derivative 011 relates to apoptosis of cell or not. Genomic DNA from cells treated with indirubin derivative 011 is isolated and fragmented.

Figure 2:
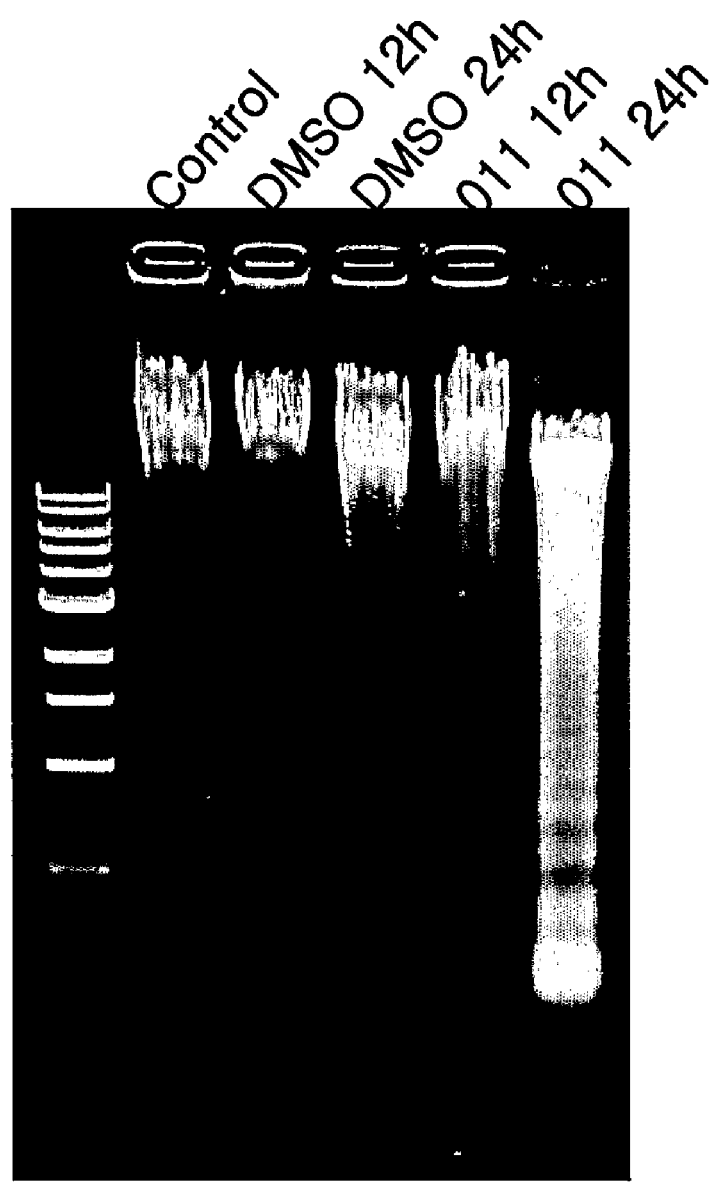
FIG. 2 is an electrophoresis photography indicating DNA fragmentation of cell line treated with indirubin derivative 011 represented by formula (I).

RK3E-Ras cell, 6×10$^5$/well is seeding on 6 well plate. After incubation of cells for 12~24 hours, 10 µM of indirubin derivative 011 is treated with cells. As a control, cells without treating any compound or cells treating DMSO in same concentration are employed. After 12 or 24 hours from treatment of drug, genomic DNA is isolated and it is loaded in 1.5% agarose gel. In the cells without treating any compound or cells treating DMSO, DNA fragmentation does not occur. However, in the cells treating indirubin derivative 011 for 12 hours, some DNA fragmentation occurs, while in the cells treating indirubin derivative 011 for 24 hours, clear DNA fragmentation is detected. FIG. 2 is a electrophoresis photography showing DNA fragmentation of cell line treated with indirubin derivative 011 represented by formula (I).

Figure 3:
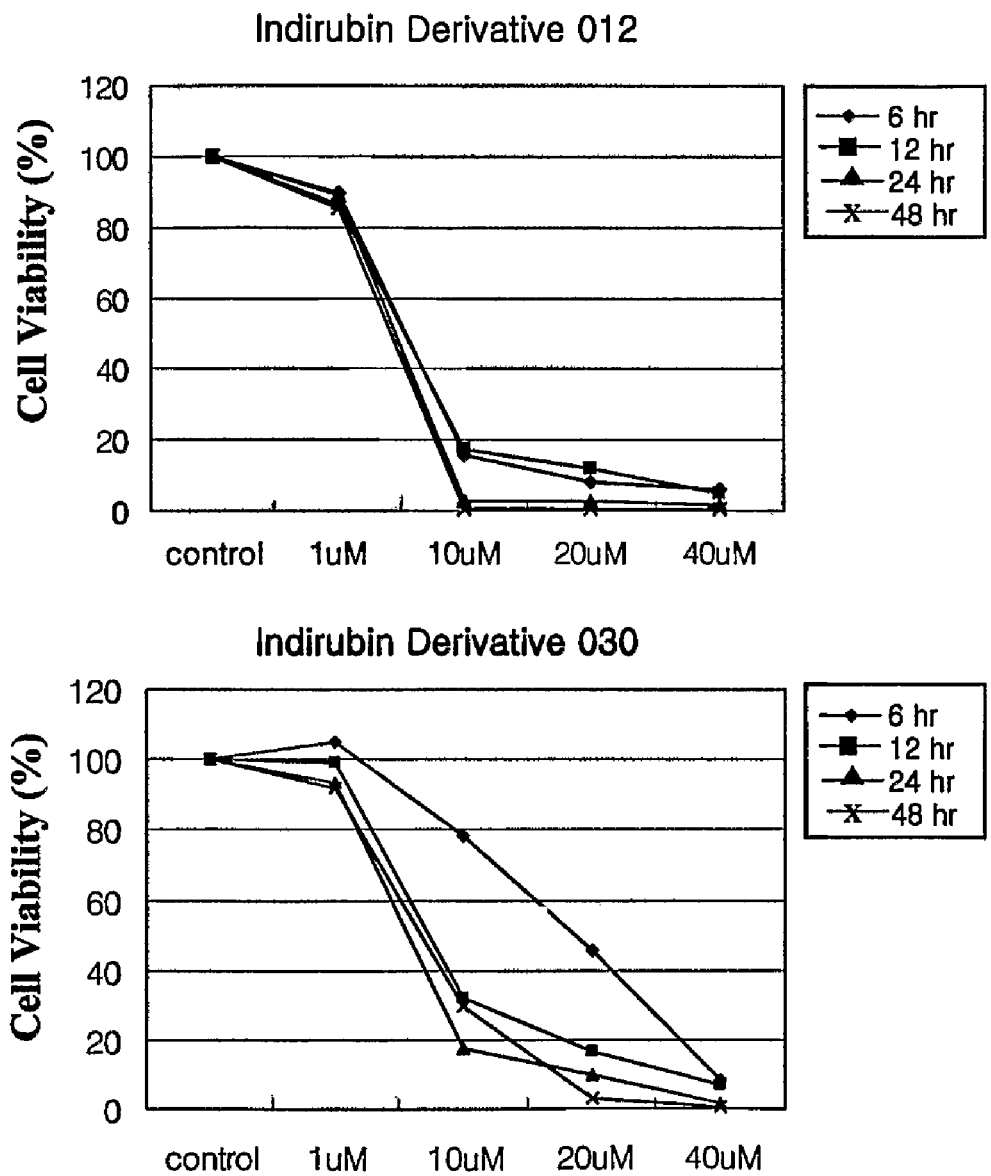
FIG. 3 is a diagram indicating the decline of cell viability according to the increase of compound concentration of indirubin derivative 012 represented by formula (II) and indirubin derivative 030 represented by formula (VI).

According to the same condition in Example 3, other indirubin derivative 012, 030 are treated to measure the influence to cell viability. Indirubin derivative 012, 030 also show rapid decline of cell viability according to increase of compound concentration. FIG. 3 shows a diagram indicating the decline of cell viability according to the increase of concentration of indirubin derivative 012 represented by formula (II) and indirubin derivative 030 represented by formula (VI).

Example 5

Annexin-V-FLUOS/propidium Iodide Double Staining Assay for Apoptosis

Annexin-V-FLUOS/propidium iodide double staining assay is a sensitive method for measuring apoptosis in cell level by detecting exposed phosphatidyl serine in apoptotic cell membrane.

Figure 4:
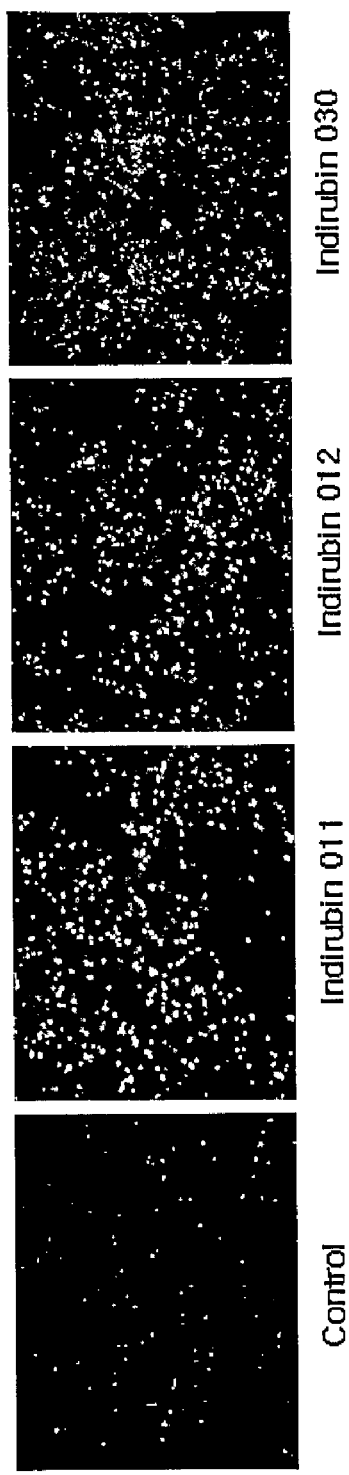
FIG. 4 is a photography showing annexin-V-FLUOS/propidium iodide double staining assay indicating apoptosis by indirubin derivative 011, indirubin derivative 012 and indirubin derivative 030 of present invention.

RK3E-Ras cell is seeding in 6×10$^5$ level on cover side. Indirubin derivatives 011, 012 and 030 are treated in 1 µM concentration for 24 hours. As a control, cells without treating any compound are employed. After 24 hours, cells are annexin-V-FLUOS/propidium iodide double stained using annexin-V-FLUOS staining kit. After detecting by fluorescent microscope, cells treated with indirubin derivatives 011, 012 and 030 are far more stained by green fluorescence than cells of control group. It is confirmed that apoptosis of cells treated with indirubin derivatives 011, 012 and 030 is processed. As shown in FIG. 4, apoptosis treated with indirubin derivative 011 is fast processed. FIG. 4 shows a photography after annexin-V-FLUOS/propidium iodide double staining as to cells treated with indirubin derivatives 011, 012 and 030.

Example 6

Indirubin Derivatives Inhibited the Tumor Progression

RK3E cell is one of rat kidney cell and it is immortalized by EA1 oncogene. It shows a normal karyotype and it does not have tumorigenic effect in nude rat. Inventors prepares stable RK3E-k-ras cell line by infection of retroviral expression vector to express mutant k-ras of oncogene. Prepared cell line is intramuscularly infected to Sprague Dawley rat to induce tumor. It is observed that solid tumor is formed and transferred into abdominal cavity within 2 weeks. Tumor suppression effect by indirubin derivatives 011, 012 and 030 is measured through tumor induced rats.

$1 \times 10^7$ of RK3E-ras cells is injected to Sprague Dawley rat to induce solid tumor for 5 days and experimental groups of animals are employed by size and volume of tumor in these animals. 100 mM of indirubin derivative is injected to experimental group of animals 5 times in every other day.

Figure 5:
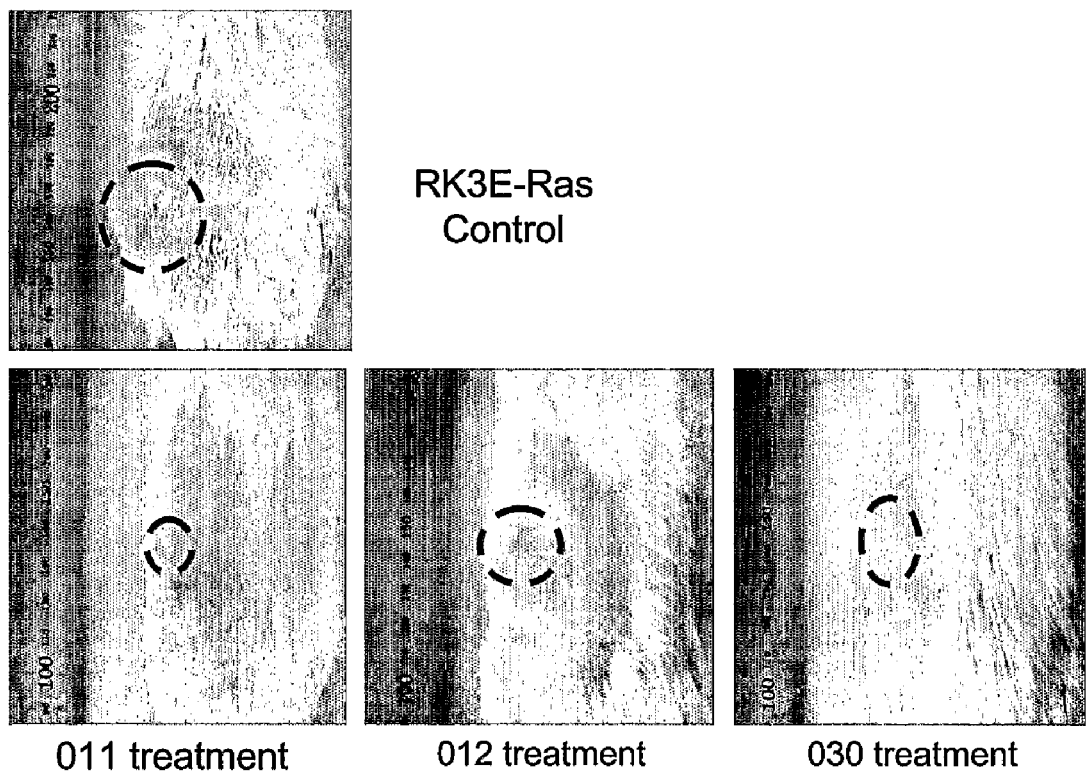
FIG. 5 is an in vivo photography indicating the inhibition of tumor proliferation according to indirubin derivative 011, 012, 030 of present invention.

As a result, it is observed that the size and volume of tumor in control group increase, while the size and volume of tumor in injecting group by indirubin derivatives 011, 012 and 030 decrease. FIG. 5 shows in vivo photography indicating the suppression of tumor proliferation according to indirubin derivatives 011, 012 and 030.

Example 7

Measurements of Rat Tumor Volume after Treatment of Indirubin Derivatives (011, 012 and 030)

Figure 6:
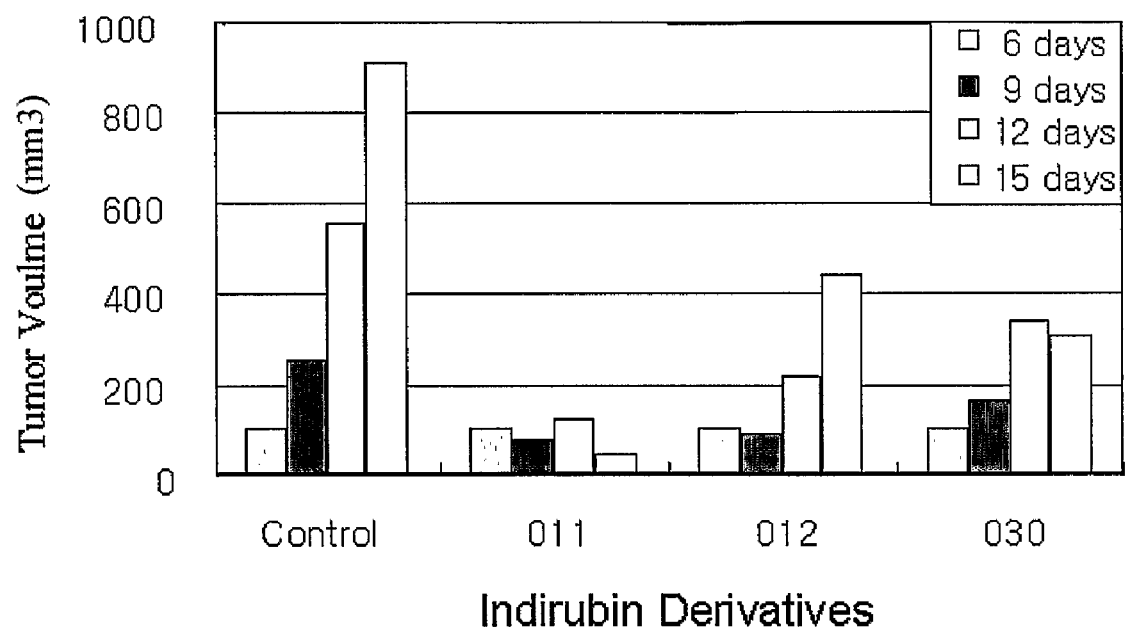
FIG. 6 is a diagram indicating the decline of cancer volume after treating indirubin derivative 011, 012, 030 of present invention.

Tumor is measured by vernier caliper and the volume of tumor is calculated by Carlsso calculation method {V=1/2 (a.b$^2$), a: long axis, b: short axis}. After measuring the volume of tumor, indirubin derivatives 011, 012 and 030 are effective for suppressing rat tumor. Especially, indirubin derivative 011 shows 80% of suppression against tumor whereas indirubin derivatives 012 and 030 show 50~60% of suppression. As a result, it is confirmed that indirubin derivatives 011, 012 and 030 are effective suppressor. FIG. 6 is a diagram showing the decline of cancer volume after treating indirubin derivatives 011, 012 and 030.

Example 8

Softex-X-ray Analysis After Treatment of Indirubin Derivatives in vivo

Figure 7:
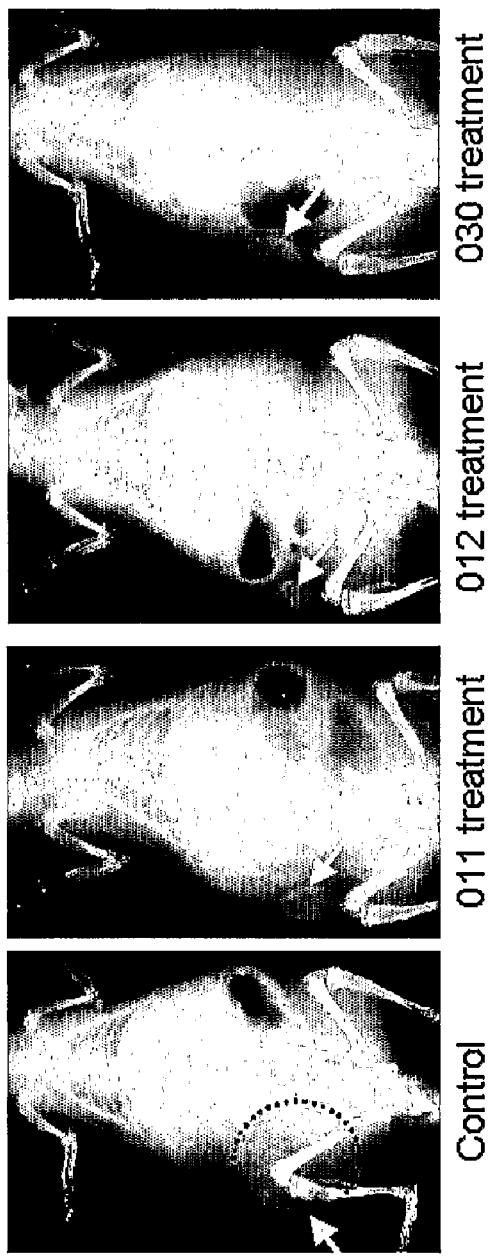
FIG. 7 is a Softex-X-ray photography after treating indirubin derivative 011, 012, 030 of present invention.

Softex-X-ray analysis is carried out after 10 days from treatment of indirubin derivatives to rat solid tumor. Calcification in tumor treated with indirubin derivatives is observed, while the volume of tumor in control group is continuously increasing. FIG. 7 is Softex-X-ray photography after treating indirubin derivatives 011, 012 and 030.

Example 9

Histological Appearance of Tumor Lesion After Indirubin Derivatives Treatment

Figure 8:
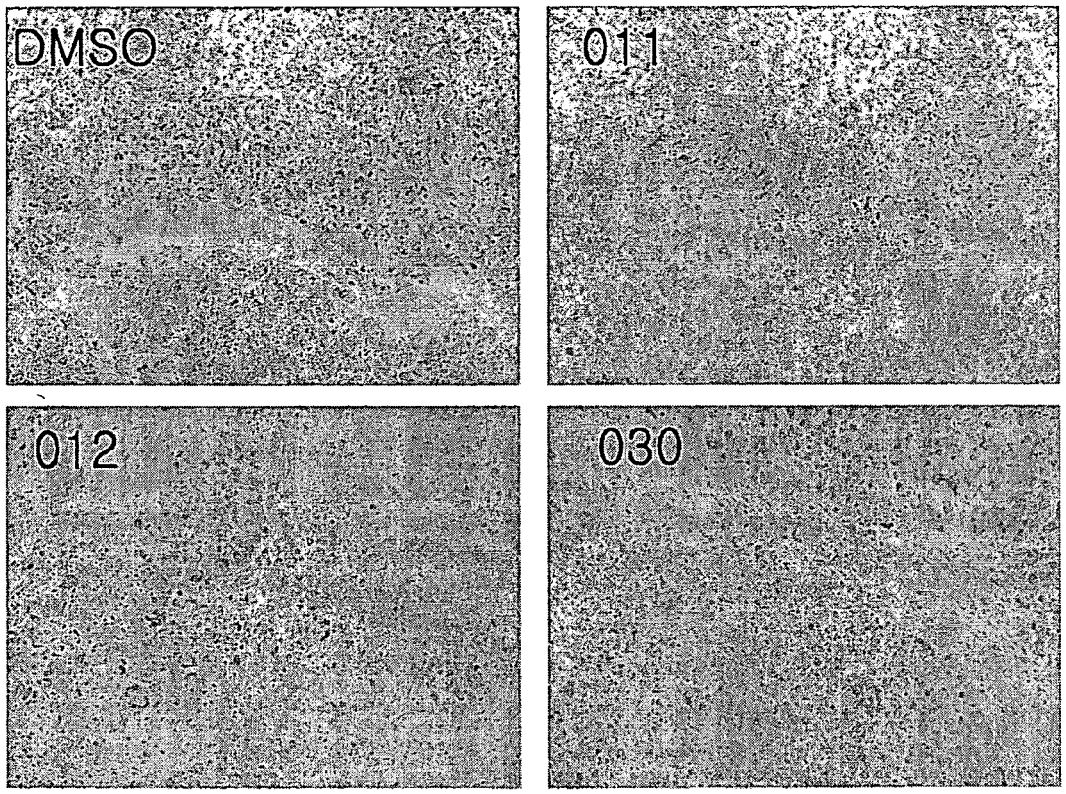
FIG. 8 is a photography of cancer lesion after treating indirubin derivative 011, 012, 030 of present invention.

To observe histological appearance of tumor lesion after indirubin derivatives 011, 012 and 030 treatment, tumor tissue is immobilized in para-formaldehyde solution and is treated with paraffin. Then, H&E stain is carried out. In the tumor only treated with DMSO, lots of amount of tumor cells remain, whereas necrosis or calcification of tumor is observed as to the tumor treated with indirubin derivatives 011, 012 and 030. From this experiment, indirubin derivatives of the present invention induce apoptosis of tumor, which results in the suppression of tumor formation in tissue level. FIG. 8 is photography showing the appearance of tumor lesion after treating indirubin derivatives 011, 012 and 030 of present invention.

The advantageous effect of present invention is to afford excellent anti-cancer agent representing AGM011, AGM029, AGM012, AGM014, AGM030 and AGM031. These compounds show far excellent anti-cancer property which cannot be anticipated from conventional indirubin compound.

What is claimed is:

1. An indirubin compound having the following formula:

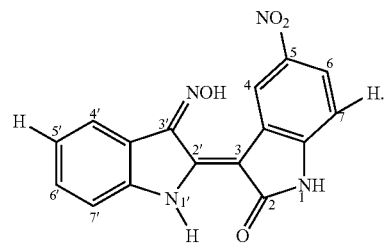

2. An indirubin compound having the following formula:

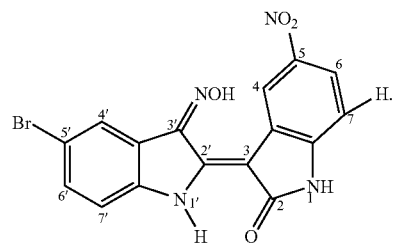

3. An indirubin compound having the following formula:

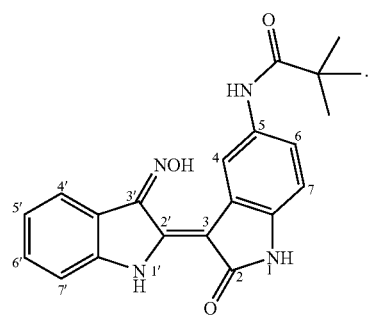

4. A composition comprising 0.1-80 wt % of the compound of claim 1 and a pharmaceutically acceptable carrier.

5. The composition according to claim 4 in the form of an injection formulation, capsule, tablet, solution, or pellet.

6. A composition comprising 0.1-80 wt % of the compound of claim 2 and a pharmaceutically acceptable carrier.

7. The composition according to claim 6 in the form of an injection formulation, capsule, tablet, solution, or pellet.

8. A composition comprising 0.1-80 wt % of the compound of claim 3 and a pharmaceutically acceptable carrier.

9. The composition according to claim 8 in the form of an injection formulation, tablet, solution, or pellet.

* * * * *

UNITED STATES PATENT AND TRADEMARK OFFICE
CERTIFICATE OF CORRECTION

PATENT NO. : 7,572,923 B2 Page 1 of 1
APPLICATION NO. : 10/586780
DATED : August 11, 2009
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 117 days.

Signed and Sealed this

Seventh Day of September, 2010

David J. Kappos
*Director of the United States Patent and Trademark Office*